(12) United States Patent
Weiss

(10) Patent No.: US 7,704,737 B2
(45) Date of Patent: Apr. 27, 2010

(54) OLIGODENDROCYTE PRODUCTION FROM MULTIPOTENT NEURAL STEM CELLS

(75) Inventor: Samuel Weiss, Calgary (CA)

(73) Assignee: Stem Cell Therapeutics Inc., Calgary, AB ( * ) Notice: Subject to any disclaimer, the term of this patent is extended or adjusted under 35 U.S.C. 154(b) by 416 days.

(21) Appl. No.: 10/523,253

(22) PCT Filed: Jul. 30, 2003

(86) PCT No.: PCT/CA03/01151

§ 371 (c)(1),
(2), (4) Date: Jan. 26, 2005

(87) PCT Pub. No.: WO2004/011632

PCT Pub. Date: Feb. 5, 2004

(65) Prior Publication Data

US 2005/0244965 A1 Nov. 3, 2005

Related U.S. Application Data

(60) Provisional application No. 60/399,192, filed on Jul. 30, 2002.

(51) Int. Cl.
 C12N 5/08 (2006.01)
 C12N 5/00 (2006.01)
 C12N 5/02 (2006.01)
(52) U.S. Cl. .............. 435/377; 435/383; 435/385; 435/325; 435/368
(58) Field of Classification Search ............ 435/377, 435/383, 385, 325, 368
See application file for complete search history.

(56) References Cited

U.S. PATENT DOCUMENTS

| | | | |
|---|---|---|---|
| 5,128,242 A | 7/1992 | Arimura et al. | |
| 5,198,542 A | 3/1993 | Onda et al. | |
| 5,208,320 A | 5/1993 | Kitada et al. | |
| 5,326,860 A | 7/1994 | Onda et al. | |
| 5,547,935 A | 8/1996 | Mullenbach et al. | |
| 5,623,050 A | 4/1997 | Kitada et al. | |
| 5,750,376 A | 5/1998 | Weiss et al. | |
| 5,801,147 A | 9/1998 | Kitada et al. | |
| 5,851,832 A | 12/1998 | Weiss et al. | |
| 5,955,346 A | 9/1999 | Wells et al. | |
| 5,980,885 A | 11/1999 | Weiss et al. | |
| 6,191,106 B1 | 2/2001 | Mullenbach et al. | |
| 6,242,563 B1 | 6/2001 | Dong | |
| 6,429,186 B1 | 8/2002 | Fuh et al. | |
| 6,673,606 B1 * | 1/2004 | Tennekoon et al. | 435/372 |
| 6,897,060 B1 * | 5/2005 | Bjornson et al. | 435/325 |
| 2002/0151488 A1 | 10/2002 | Sarkar et al. | |
| 2002/0198150 A1 | 12/2002 | Chajut | |
| 2003/0171269 A1 * | 9/2003 | Magil et al. | 514/12 |
| 2004/0120925 A1 | 6/2004 | Toda et al. | |
| 2004/0141946 A1 | 7/2004 | Schaebitz et al. | |
| 2004/0141947 A1 | 7/2004 | Hunter | |
| 2005/0142102 A1 | 6/2005 | Schaebitz et al. | |
| 2007/0048255 A1 | 3/2007 | Hunter | |
| 2008/0175894 A1 | 7/2008 | Schaebitz et al. | |
| 2008/0286234 A1 | 11/2008 | Eyink | |

FOREIGN PATENT DOCUMENTS

| | | |
|---|---|---|
| DE | 10033219 | 1/2002 |
| WO | WO 94/10292 | 11/1994 |
| WO | WO 9513394 | 5/1995 |
| WO | WO 96/15226 | 5/1996 |
| WO | WO 00/00588 | 1/2000 |
| WO | WO 0166698 | 9/2001 |
| WO | WO 01/78753 | 10/2001 |
| WO | WO 03/040310 | 5/2003 |
| WO | WO 2004/035086 | 4/2004 |

OTHER PUBLICATIONS

Imitola J, Snyder EY, Khoury SJ. Genetic programs and responses of neural stem/progenitor cells during demyelination: potential insights into repair mechanisms in multiple sclerosis. Physiol Genomics. Aug. 15, 2003;14(3):171-97.*

Chandran S, Compston A. Neural stem cells as a potential source of oligodendrocytes for myelin repair. J Neurol Sci. Jun. 15, 2005;233(1-2):179-81.*

Evans et al. (Blood, 2002. vol. 100, No. 9, pp. 3164-3174).*

Deng, X., and Sriram, S. (2005). Role of microglia in multiple sclerosis. Curr Neurol Neurosci Rep. 5(3):239-244.

Hamilton, S.P., et al. (1995). Microglical-derived GM-CSF stimulates oligodendrocyte function in the central nervous system. Blood 86:25A XP009056228 37th Annual Meeting of the American Society of Haematology; Seattle, Washington, US, Dec. 1-5, 1995.

(Continued)

*Primary Examiner* — Thaian N Ton
(74) *Attorney, Agent, or Firm* — Fish & Richardson P.C.

(57) ABSTRACT

This invention relates to methods of producing oligodendrocytes from multipotent neural stem cells by using at least one oligodendrocyte promoting factor, particularly granulocyte-macrophage colony stimulating factor, granulocyte colony stimulating factor, interleukin 3 or interleukin 5. The neural stem cells may optionally be expanded prior to being subjected to the oligodendrocyte promoting factor.

15 Claims, 6 Drawing Sheets

OTHER PUBLICATIONS

Sawada, M., et al. (1993). Expression of cytokine receptors in cultured neuronal and glial cells. Neurosci Lett. 160(2):131-134.
Bernichtein, S., et al. (2001). S179D-human PRL, a pseudophosphorylated human PRL analog, is an agonist and not an antagonist. Endocrinology. 142(9):3950-3963.
Brierley, C.M., et al. (2001). Remyelination of demyelinated CNS axons by transplanted human schwann cells: the deleterious effect of contaminating fibroblasts. Cell Transplant. 10(3):305-315.
DuBois, T.M., and Weiss, S., "Granulocyte Macrophage—Colony Stimulating Factor (GM—CSF) is a Fate Determination and Differentiation Factor for Neural Stem Cell—Generated Oligodendrocyte Precursors (OLPS)." Database BIOSIS 'Online! Biosciences Information Service, Philadelphia, PA, US; 2002 and Society for Neuroscience Abstract Viewer and Itinerary Planner, vol. 2002, pages Abstract No. 329.12 URL: http://sf,32ndannualmeetingofthesocietyforneuroscience; Orlando; Florida; USA; Nov. 2-7, 2002.
Gage, F.H. (2000). Mammalian neural stem cells. Science. 287(5457):1433-1438.
Kohama, I., et al. (2001). Transplantation of cryopreserved adult human Schwann cells enhances axonal conduction in demyelinated spinal cord. J Neurosci. 21(3):944-950.
Learish, R.D., et al. (1999). Intraventricular transplantation of oligodendrocyte progenitors into a fetal myelin mutant results in widespread formation of myelin. Ann Neurol. 46(5):716-722.
McLay, R.N., (1997) Granulocyte-macrophage colony-stimulating factor crosses the blood—brain and blood—spinal cord barriers. Brain. 120 (Pt 11):2083-2091.
McQualter, J.L., et al. (2001). Granulocyte macrophage colony-stimulating factor: a new putative therapeutic target in multiple sclerosis. J Exp Med. 194(7):873-882.
Mehler, M.F., et al. (1995). Cytokines regulate the cellular phenotype of developing neural lineage species. Int J Dev Neurosci. 13(3-4):213-240.
Miller, R.H. (2002). Regulation of oligodendrocyte development in the vertebrate CNS. Prog Neurobiol. 67(6):451-467.
Ousman, S.S., and David, S. (2001). MIP-1α, MCP-1, GM-CSF, and TNF-α control the immune cell response that mediates rapid phagocytosis of myelin from the adult mouse spinal cord. J Neurosci. 21(13):4649-4656.
Raff, M.C. (1989). Glial cell diversification in the rat optic nerve. Science. 243(4897):1450-1455.
Smith, P.M., and Franklin, R.J. (200). The effect of immunosuppressive protocols on spontaneous CNS remyelination following toxin-induced demyelination. J Neuroimmunol. 119(2):261-268.
Gumpel et al., "Myelination and remyelination in the central nervous system by transplanted oligodendrocytes using the shiverer model" Dev. Neurosci. 11:132-139 (1989).
Hierholzer et al., "Activation of STAT proteins following ischemia reperfusion injury demonstrates a distinct IL-6 and G-CSF mediated profile" Transplantation Proceedings 30(6):2647 (1998).
Konishi et al., "Trophic effect of erythropoietin and other hematopoietic factors on central cholinergic neurons in vitro and in vivo" Brain Research 609(1-2):29-35 (1993).
Mehler et al., "Developmental changes in progenitor cell responsiveness to bone morphogenetic proteins differentially modulate progressive CNS lineage fate" Developmental Neuroscience 22:74-85 (2000).
Schaebitz et al., "Recombinant granulocyte-colony stimulating factor (RG-CSF) is neuroprotective following focal transient cerebral ischemia and excitotoxicity" Society for Neuroscience Abstracts, Society for Neuroscience 27(Part 2):2027 (2001).

Schaebitz et al., "Neuroprotective effect of granulocyte colony-stimulating factor after focal cerebral ischemia" Stroke 34(3):745-751 (2003).
Smith et al., "Macrophage and microglial responses to cytokines in vitro: phagocytic activity, proteolytic enzyme release, and free radical production" Journal of Neuroscience Research 54:68-78 (1998).
Temple "The development of neural stem cells" Nature 414:112-116 (2001).
Tian et al., "Multiple signaling pathways induced by granulocyte colony-stimulating factor involving activation of JAKs, STAT5 and/or STAT3 are required for regulation of three distinct classes of immediate early genes" Blood 88(12):4435-4444 (1996).
Ward et al., "Tyrosine-dependent and -independent mechanisms of STAT3 activation by the human granulocyte cology-stimulating factor (G-CSF) receptor are differentially utilized depending on G-CSF concentration" Blood 93(1):113-124 (1999).
Baldwin, G.C., "Identification and Characterization of a High-Affinity Granulocyte-Macrophage Colony-Stimulating Factor Receptor on Primary Rat Oligodendrocytes" Blood, vol. 82, No. 11, pp. 3279-3282, Dec. 1, 2007.
Barclay, Laurie. "Immune-Enhancer GM-CSF Helpful in Crohn's Disease". Lancet. 360: 1478-1479. Nov. 8, 2002.
Marusic, S. et al., "Local delivery of granulocyte macrophage colony-stimulating factor by retrovirally transduced antigen-specific T cells leads to severe, chronic experimental autoimmune encephalomyelitis in mice." Neuroscience Letters, vol. 332, No. 3: 185-189, Nov. 8, 2002.
Maurer, M.H. et al., "Old friends in new constellations—the hematopoetic growth factors G-CSF, GM-CSF, and EPO for the treatment of neurological diseases." Current Medicinal Chemistry, vol. 15, No. 14: 1407-1411, 2008.
Pitzer, C. et al., "Granulocyte-colony stimulating factor improves outcome in a mouse model of amyotrophic lateral sclerosis." Brain, vol. 131, No. pt. 12: 3335-3347, Dec. 2008.
Rutella, S. et al., "Granulocyte colony-stimulating factor: a novel mediator of T cell tolerance." Journal of Immunology, vol. 175, No. 11: 7085-7091, Dec. 1, 2005.
Snir, O. et al., "G-CSF enhances the adhesion of encephalitogenic T cells to extracellular matrix components: a possible mechanism for exacerbation of multiple sclerosis." Journal of Neuroimmunology, vol. 172, No. 1-2: 145-155, Mar. 2006.
Zavala, F. et al., "G-CSF therapy of ongoing experimental allergic encephalomyelitis via chemokine-and cytokine-based immune deviation." Journal of Immunology, vol. 168, No. 4: 2011-2019, Feb. 15, 2002.
Baldwin et al., "Identification and Characterization of High-Affinity Granulocyte-Macrophage Colony-Stimulating Factor Receptor on Primary Rat Oligodendrocytes," Blood vol. 82, No. 11, pp. 3279-3282. Dec. 1, 1993.
Ha et al., "Role of granulocyte-macrophage colony-stimulating factor in preventing apoptosis and improving functional outcome in experimental spinal cord contusion injury," J. Neurosurg Spine vol. 2, pp. 55-61. Jan. 2005.
English translation of Itoh et al., "Expression of cytokine receptor from cultured glial cells and nervous cells," The Japanese Society for Neurochemistry, vol. 32 No. 1, pp. 38-39 Oct. 12, 1993.
Sawada et al., "Expression of cytokine receptors in cultured neuronal and glial cells," Neuroscience Letters, 160 (1993) 131-134.
Tosic et al., "Triiodothyronine Has Diverse and Multiple Stimulating Effects on Expression of the Major Myelin Protein Genes," Journal of Neurochemistry vol. 59, No. 5, pp. 1770-1777 (1992).

\* cited by examiner

OLIGODENDROCYTE PRODUCTION FROM MULTIPOTENT NEURAL STEM CELLS

RELATED APPLICATIONS

This application is the national phase application of International Application No. PCT/CA2003/001151, filed Jul. 30, 2003, which claims the benefit of U.S. Provisional Application Ser. No. 60/399,192, filed Jul. 30, 2002. The entire disclosure of each of the prior applications is incorporated herein by reference in its entirety.

FIELD OF THE INVENTION

This invention relates to methods of producing, oligodendrocytes by using an oligodendrocyte promoting factor, particularly granulocyte-macrophage colony stimulating factor, granulocyte colony stimulating factor, interleukin 3 or interleukin 5.

REFERENCES

U.S. Pat. No. 5,128,242.
U.S. Pat. No. 5,198,542.
U.S. Pat. No. 5,208,320.
U.S. Pat. No. 5,326,860.
U.S. Pat. No. 5,547,935.
U.S. Pat. No. 5,623,050.
U.S. Pat. No. 5,750,376.
U.S. Pat. No. 5,801,147.
U.S. Pat. No. 5,851,832.
U.S. Pat. No. 5,955,346.
U.S. Pat. No. 5,980,885.
U.S. Pat. No. 6,191,106.
U.S. Pat. No. 6,242,563.
U.S. Pat. No. 6,429,186.
WO 03/040310. Be'eri H et al. The cytokine network of wallerian degeneration: IL-10 and GM-CSF. Eur. J. Neurosci. 10(8):2707-13 (1998).

Bernichtein, S., et al. S179D-human PRL, a pseudophosphorylated human PRL analog, is an agonist and not an antagonist. Endocrinology 142(9):3950-3963 (2001).

Brierley C M et al. Remyelination of demyelinated CNS axons by transplanted human schwann cells: the deleterious effect of contaminating fibroblasts. Cell Transplant. 10(3): 305-15 (2001).

Kohama I et al. Transplantation of cryopreserved adult human Schwann cells enhances axonal conduction in demyelinated spinal cord. J. Neurosci. 21(3):944-50 (2001).

Learish R D et al. Intraventricular transplantation of oligodendrocyte progenitors into a fetal myelin mutant results in widespread formation of myelin. Ann. Neurol. 46(5):716-722 (1999).

McLay R N et al. Granulocyte-macrophage colony-stimulating factor crosses the blood-brain and blood-spinal cord barriers. Brain 120:2083-2091 (1997).

Miller R H. Regulation of oligodendrocyte development in the vertebrate CNS. Progress in Neurobiology 67: 451-467 (2002).

Ousman S S et al. MIP-1alpha, MCP-1, GM-CSF, and TNF-alpha control the immune cell response that mediates rapid phagocytosis of myelin from the adult mouse spinal cord. J. Neurosci. 21(13):4649-4656 (2001).

Raff M C. Glial cell diversification in the rat optic nerve. Science 243(4897):1450-5 (1989).

Smith P M and Franklin R J. The effect of immunosuppressive protocols on spontaneous CNS remyelination following toxin-induced demyelination. J. Neuroimmunol. 119(2-): 261-8 (2001).

All of the publications, patents and patent applications cited in this application are herein incorporated by reference in their entirety to the same extent as if the disclosure of each individual publication, patent application or patent was specifically and individually indicated to be incorporated by, reference in its entirety.

BACKGROUND OF THE INVENTION

The axons of manly vertebrate neurons are insulated by a myelin sheath, which greatly increases the rate at which axons can conduct an action potential. Myelin is a cellular sheath formed by special glial cells, namely Schwann cells in the peripheral nervous system and oligodendrocytes in the central nervous system. These glial cells wrap layer upon layer around the axon in a tight spiral, thereby insulating the axonal membrane. However, the sheath is interrupted at regularly spaced nodes of Ranvier, where membrane depolarization can occur. As a result, depolarization of the membrane at one node immediately spreads to the next node. Thus, an action potential propagates along a myelinated axon by jumping from node to node, thereby accelerating transmission of the signal as well as conserving metabolic energy, since the active excitation is confined to the small regions of axonal plasma membrane at the nodes.

The importance of myelination is evidenced by demyelinating diseases such as multiple sclerosis, in which myelin sheaths in some regions of the central nervous system are destroyed by an unknown mechanism. When demyelination occurs, the propagation of nerve impulses is significantly slowed, leading to devastating neurological consequences. For example, common symptoms of multiple sclerosis include muscular weakness, slow movements, spasticity, severe fatigue or even disabling exhaustion, visual disturbances, pain, numbness, tingling, urinary dysfunction, sexual dysfunction and mental disturbances.

Current treatments of multiple sclerosis involve slowing down the disease course as well as alleviation of the symptoms or medical complications, rather than addressing the underlying cause of the disease, demyelination. Howsoever, ample evidence indicates that demyelinated neurons are capable of remyelination in siru. In multiple sclerosis, it appears that cycles of demyelination and remyelination take place, and glial cell transplantation has been investigated as a potential therapy (see, e.g., Smith et al., 2001; Brierley et al., 2001: Kohama et al., 2001). Nevertheless, obtaining large numbers of myelinating cells for transplantation remains a major stumbling block. Glial progenitor cells are available for transplantation; for example, O-2A cells give rise in vitro to oligodendrocytes and type II astrocytes. Although O-2A cells can be grown in culture, only a limited number of divisions are possible (Raff, 1989). Moreover, it appears that the O-2A cells that have been injected into animals do not continue to divide, and a large number of cells have to be transplanted. Therefore, an improved source of transplant for remyelination is desirable.

SUMMARY OF THE INVENTION

The present invention relates to methods of producing oligodendrocytes from multipotent neural stem cells by using an oligodendrocyte promoting factor, particularly granulocyte-macrophage colony stimulating factor (GM-CSF), granulocyte colony stimulating factor (G-CSF), interleukin 3 (IL-3) or interleukin 5 (IL-5). We demonstrate herein that these factors, such as GM-CSF, significantly increased the percentage of oligodendrocytes produced from neural stem cells. When GM-CSF was present in the proliferation media of neural stem cells, proliferating neural stem cells were decreased while oligodendrocytes were increased. Therefore, GM-CSF can shift fate determination of neural stem cells toward the oligodendrocyte lineage. To maximize oligodendrocyte production, it is preferable to enhance neural stem cell proliferation first, followed by subjecting the expanded neural stem cells to the oligodendrocyte promoting factor to increase oligodendrocyte formation.

The present invention further provides a method of producing oligodendrocytes in vivo by administering at least one oligodendrocyte promoting factor to a mammal. This method can be used to enhance myelination, particularly remyelination in a mammal with a demyelinating disease. Accordingly, the present invention also provides a method of treating or ameliorating a demyelinating disease by using an oligodendrocyte promoting factor.

Accordingly, one aspect of the present invention provides a method of producing oligodendrocytes from mammalian multipotent neural stem cells, comprising contacting multipotent neural stem cells with an effective amount of at least one oligodendrocyte promoting factor under conditions that result in production of oligodendrocytes from the multipotent neural stem cells. The oligodendrocyte promoting factor is preferably selected from the group consisting of GM-CSF, G-CSF, IL-3 and IL-5. The oligodendrocyte promoting factor is more preferably GM-CSF or G-CSF, and is most preferably GM-CSF.

The neural stem cells can be any mammalian neural stem cells, including, for example, human, feline, canine, rodent, sheep, goat, cattle, horse, pig, and non-human primate cells. The neural stem cells are preferably human cells.

The method can be practiced in vitro vivo. For the in vitro method, the neural stem cells may be provided as a cell culture, and the oligodendrocyte promoting factor can be included in the culture medium. The culture is preferably prepared by using mammalian brain tissue obtained from any mammal, including embryonic, neonatal and adult mammals. In particular, the brain tissue is obtained from a non-embryonic mammal, preferably an adult mammal. The brain tissue is preferably the subventricular zone in the forebrain.

For the in vivo method, the neural stem cells are located in a mammal, particularly in the subventricular zone. The mammal preferably harbors a demyelinating disease, such as a disease selected from the group consisting of multiple sclerosis, acute disseminated encephalomyelitis, diffuse cerebral sclerosis, necrotizing hemorrhagic encephalitis and leukodystrophies. The disease is preferably multiple sclerosis.

Optionally, the neural stem cells are also subjected to at least one biological agent that is capable of increasing the number of multipotent neural stem cells. The biological agent is preferably selected from the group consisting of epidermal growth factor (EGF), pituitary adenylate cyclase-activating polypeptide (PACAP), fibroblast growth factor (FGF), transforming growth factor α(TGFα), ciliary neurotrophic factor (CNTF), estrogen, ovarian hormone, prolactin, growth hormone, and insulin-like growth factor 1. The neural stem cells are preferably contacted by the biological agent first to increase the number of neural stem cells before being subjected to the oligodendrocyte promoting factor. Alternatively, the neural stem cells may be contacted by the biological agent and the oligodendrocyte promoting factor concurrently.

Furthermore, others factors that promote oligodendrocyte differentiation, growth, proliferation or survival can also be used in combination with the oligodendrocyte promoting factor. A preferred example of such other factors is triiodothyronine.

Another aspect of the present invention provides a composition comprising the oligodendrocytes produced from neural stem cells by using at least one oligodendrocyte promoting factor. The composition may optionally comprise a pharmaceutically acceptable excipient and/or a pharmaceutically acceptable carrier to form a pharmaceutical composition.

Also provided is a method of providing oligodendrocytes to a mammal, comprising (a) introducing multipotent neural stem cells into the mammal and administering an effective amount of at least one oligodendrocyte promoting factor to the mammal under conditions that result in oligodendrocyte formation from the neural stem cells; or b) introducing into the mammal an effective amount of the pharmaceutical composition described above.

When method (a) is employed, the neural stem cells can be further contacted, either prior to the introduction or after the introduction occurs, by at least one biological agent that is capable of increasing the number of neural stem cells. It is also contemplated that the biological agent can be used both before and after transplantation. The agent can be added to the culture media before transplantation and/or administered to the mammal after transplantation.

Another aspect of the present invention provides a method of treating or ameliorating a demyelinating disease in a mammal, comprising administering to the mammal an effective amount of at least one oligodendrocyte promoting factor. The mammal preferably harbors a demyelinating disease, such as a disease selected from the group consisting of multiple sclerosis, acute disseminated encephalomyelitis, diffuse. cerebral sclerosis, necrotizing hemorrhagic encephalitis and leukodystrophies. The disease is preferably multiple sclerosis. The mammal may, additionally receive at least one biological agent that is capable of increasing the number of neural stem cells, and/or at least one factor that is known to stimulate oligodendrocyte differentiation, growth, proliferation or surival. The oligodendrocyte promoting factor, the biological agent. and/or other factors can be administered in any manner that results in contact of the factor and or agent with multipotent neural stem cells in the mammal, such as systemically (e.g. . subcutaneously) or in situ (e.g., administered into the brain, particularly a lateral ventricle of the brain).

DETAILED DESCRIPTION OF THE INVENTION

Figure 1:
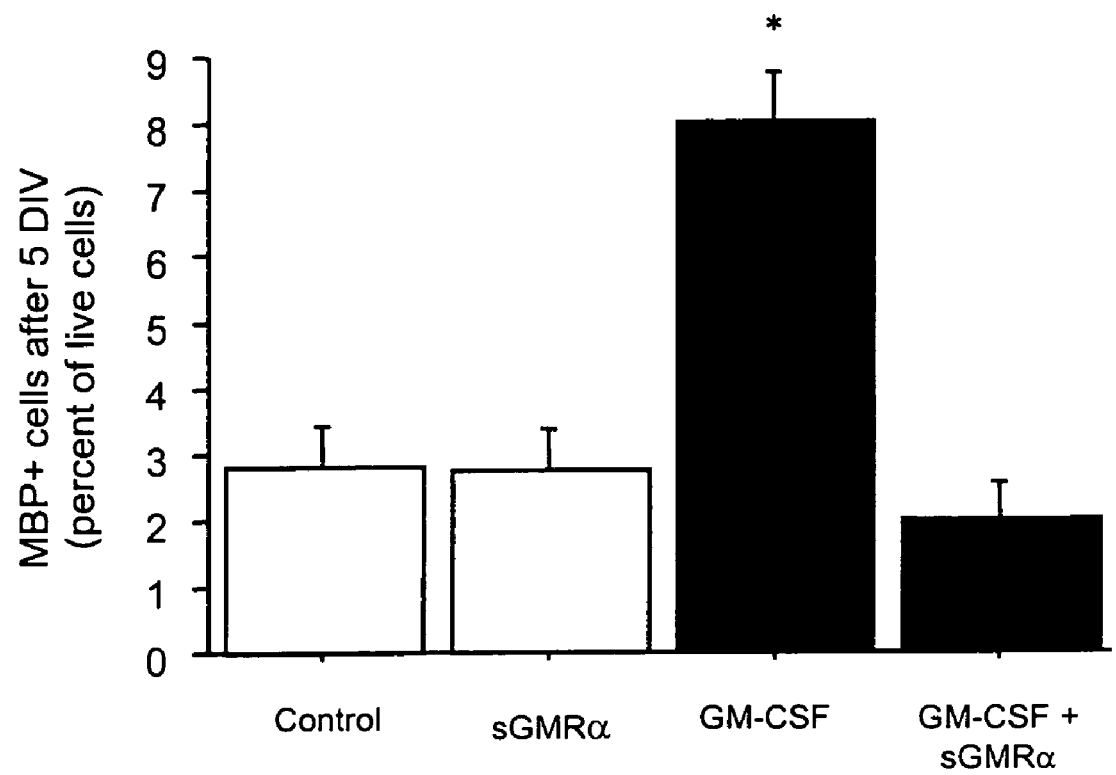
FIG. 1. A soluble GM-CSF receptor (sGMRα) inhibits the effects of GM-CSF. DIV: days in vitro.*p<0.001. The experiments were repeated 4 times (N=4).

The present invention relates to methods of producing oligodendrocytes from multipotent neural stem cells by using at least one oligodendrocyte promoting factor, particularly granulocyte-macrophage colony stimulating factor (GM-CSF), granulocyte colony stimulating factor (G-CSF), interleukin 3 (IL-3) or interleukin 5 (IL-5). We demonstrate herein that GM-CSF significantly increased the percentage of oligodendrocytes produced from neural stem cells. When GM-CSF was present in the proliferation media of neural stem cells, proliferating neural stem cells were decreased while oligodendrocytes were increased. Therefore, GM-CSF can shift fate determination of neural stem cells toward the oligodendrocyte lineage. To maximize oligodendrocyte production, it is preferable to enhance neural stem cell proliferation first, followed by subjecting the expanded neural stem cells to the oligodendrocyte promoting factor to increase oligodendrocyte formation.

The present invention further provides a method of producing oligodendrocytes in vivo by administering at least one oligodendrocyte promoting factor to a mammal. This method can be used to enhance myelination, particularly remyelination in a mammal with a demyelinating disease. Accordingly, the present invention also provides a method of treating or ameliorating a demyelinating disease by using at least one oligodendrocyte promoting factor.

Prior to describing the invention in further detail, the terms used in this application are defined as follows unless otherwise indicated.

Definitions

A "multipotent neural stem cell", or "neural stem cell", is a stem cell in the neural cell lineage. A stem cell is a cell which is capable of reproducing itself. In other words, when a stem cell divides, at least some of the resulting daughter cells are also stem cells. Neural stem cells and their progeny are capable of differentiating into all the cell types in the neural cell lineage, including neurons, astrocytes and oligodendrocytes (astrocytes and oligodendrocytes are collectively called glial or glial cells). Therefore, the neural stem cells are multipotent neural stem cells. Multipotent neural stem cells are described, for example, in U.S. Pat. Nos. 5,750,376; 5,980,885; and 5,851,832.

The adult neural stem cells preferably refer to the neural stem cells located in or derived from the subventricular zone (SVZ) of the forebrain of adult mammals, which are different from the proliferating cells in the adult hippocampus.

The "progeny" of neural stem cells described herein refers to any and all cells derived from neural stem cells as a result of proliferation or differentiation.

A "neurosphere" is a group of cells derived from a single neural stem cell as the result of clonal expansion. Primary neurospheres are generated by plating as primary cultures brain tissue which contains neural stem cells. The method for culturing neural stem cells to form neurospheres has been described in, e.g., U.S. Pat. No. 5,750,376. Secondary neurospheres can be generated by dissociating primary neurospheres and allowing the individual dissociated cells to form neurospheres again.

An "oligodendrocyte promoting factor" is a substance that is capable of increasing oligodendrocyte formation from multipotent neural stem cells. The oligodendrocyte promoting factor is preferably selected from the group consisting of granulocyte-macrophage colony stimulating factor (GM-CSF), granulocyte colony stimulating factor (G-CSF), interleukin 3 (IL-3) and interleukin 5 (IL-5).

A "granulocyte-macrophage colony stimulating factor", or "GM-CSF" is a protein factor which (1) shares substantial sequence identity with the native human GM-CSF; and (2) possesses a biological activity of the native human GM-CSF.

A protein which shares "substantial sequence identity" with a native mammalian protein consists of at least one polypeptide that is at least about 30% identical with the native mammalian protein at the amino acid level. The protein is preferably at least about 40%, more preferably at least about 60%, yet more preferably at least about 70%, and most preferably at least about 80% identical with the native protein at the amino acid level. Thus, the protein is a variant or analog of the native protein. For example, a protein that shares a substantial sequence identity with the native human GM-CSF consists of at least one polypeptide that is at least about 30% identical with the native human GM-CSF at the amino acid level. The protein is preferably at least about 40%, more preferably at least about 60%, yet more preferably at least about 70%, and most preferably at least about 80% identical with the native human GM-CSF at the amino acid level. Thus, the term "GM-CSF" encompasses GM-CSF analogs which are the deletional, insertional, or substitutional mutants of the native GM-CSF. Furthermore, the term "GM-CSF" encompasses the GM-CSFs from other species, the naturally occurring variants, and different post-translationally modified forms (such as the glycosylated and phosphorylated forms) thereof.

The phrase "percent identity," or "% identity" with a native protein refers to the percentage of amino acid sequence in the native protein which are also found in the variant or analog when the two sequences are best aligned (including gaps). Percent identity can be determined by any methods or algorithms established in the art, such as LALIGN or BLAST. Preferably, BLAST is used to determine percent identity.

A factor possesses a "biological activity of GM-CSF" if it is capable of binding to any known GM-CSF receptor.

A "primary neurosphere" is a neurosphere generated by culturing brain tissue. Typically, the brain tissue is dissected and mechanically dissociated before being cultured in appropriate media and allowed to form neurospheres. Exemplary methods are described in, for instance. U.S. Pat. No. 5,750,376.

A "secondary neurosphere" is a neurosphere generated by dissociating (passaging) a primary neurosphere and culturing the dissociated cells under conditions which result in the formation of neurospheres from single cells.

A "mammal" is any member in the mammalian family. A mammal is preferably a primate, rodent, feline, canine, domestic livestock (such as cattle, sheep, goats, horses, and pigs), and most preferably a human.

A "demyelinating disease" is a disease or medical condition that is caused by or associated with demyelination. Examples of these diseases or conditions include multiple sclerosis (including the relapsing and chronic progressive forms of multiple sclerosis, acute multiple sclerosis, neuromyelitis optica (Devic's disease)), diffuse cerebral sclerosis (including Shilder's encephalitis periaxialis diffusa and Balo's concentric sclerosis). Demyelinating diseases also include a variety of diseases wherein demyelination is caused by viral infections, vaccines, and genetic disorders. Examples of these demyelinating diseases include acute disseminated encephalomyelitis (occuring after measles, chickenpox, rubella, influenza or mumps; or after rabies or smallpox vaccination), necrotizing hemorrhagic encephalitis (including hemorrhagic leukoencephalitis), and leukodystrophies (including Krabbe's globboid leukodystrophy, metachromatic leukodystrophy, adrenoleukodystrophy, adrenomyeloneuropathy, adrenomyeloneuropathy, Pelizaeus-Merzbacher leukodystrophy, Canavan's disease and Alexander's disease). The demyelinating disease is preferably multiple sclerosis or diffuse cerebral sclerosis, and most preferably multiple sclerosis.

"Treating, or ameliorating " means the reduction or complete removal of the symptoms of a disease or medical condition.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Methods

Methods for the isolation and in vitro culture of multipotent neural stein cells have recently been developed (for example, see U.S. Pat. Nos. 5,750,376; 5,980,885; 5,851,832). It was discovered that fetal brains can be used to isolate and culture multipotent neural stem cells in vitro. Moreover, in contrast to the long time belief that adult brain cells are not capable of replicating or regenerating brain cells, it was found that neural stem cells may also be isolated from brains of adult mammals. These stem cells, either from fetal or adult brains, are capable of self-replicating. The progeny cells can gain proliferate or differentiate into any cell in the neural cell lineage, including neurons, astrocytes and oligodendrocytes.

Most of the cells differentiated from neural stem cells are astrocytes. Therefore, although neural stem cells provide a good source of all kinds of mature or immature neural cells, using neural stem cells to produce oligodendrocytes for demyelinating diseases is normally an inefficient process. The present invention, however, provides a method of significantly increasing the efficiency of oligodendrocyte production from neural stem cells. As shown in Example 1, when neural stem cells were allowed to differentiate in the presence of granulocyte-macrophage colony stimulating factor (GM-CSF), the percentage of oligodendrocytes increased by several folds. Therefore. GM-CSF can be used to enhance oligodendrocyte production from neural stem cells. In particular, GM-CSF can be used as a survival factor for oligodendrocytes or precursors thereof (Example 2).

GM-CSF does not stimulate neural stem cells to proliferate. In fact, inclusion of GM-CSF in the proliferation media of neural stem cells inhibited self-expansion of proliferated neural stem cells (Example 3), probably by inducing premature differentiation of neural stem cells. Indeed; the neural stem cells that were exposed to GM-CSF in the presence of proliferating signal (in this case, epidermal growth factor) expressed markers for oligodendrocyte progenitor cells shortly after being shifted to differentiation media, suggesting that these cells had committed to the oligodendrocyte lineage in the proliferation media. Consistent with these results, GM-CSF inhibited commitment to the neuronal lineage (Example 4).

The present invention thus provides a method of increasing oligodendrocyte production from neural stem cells by, using an oligodendrocyte promoting factor, such as GM-CSF. Preferably, neural stem cells are first proliferated or expanded in the absence of the oligodendrocyte promoting factor, and the expanded population of neural stem cells are then incubated with the oligodendrocyte promoting factor to induce oligodendrocyte formation. Any agent capable of expanding neural stem cells can be used in this embodiment. These agents may stimulate proliferation, inhibit differentiation or prevent cell death of neural stem cells. Exemplary agents include, without being limited to, epidermal growth factor (EGF), pituitary adenylate cyclase-activating polypeptide (PACAP), fibroblast growth factor (FGF), transforming growth factor α (TGFα), estrogen, ovarian hormone, prolactin, growth hormone, insulin-like growth factor, ciliary neurotrophic factor (CNTF) and bone morphogenetic protein (BMP). Additional agents may be identified by methods known in the art, such as adding a candidate agent to a culture of neural stem cells and assessing the number of neurospheres formed in the presence of the agent (see, e.g., U.S. Pat. Nos. 5,750,376; 5,980,885; 5,851,832).

It should be noted that variants or analogs of these agents, which share a substantial identity with a native mammalian agent listed above and are capable of increasing neural stem cell numbers, can be used in the present application. For example, there are two forms of native mammalian PACAP, PACAP38 and PACAP27. Any variant or analog that is capable of increasing neural stem cell numbers and shares a substantial sequence identity with either PACAP38or PACAP27 is suitable for use in the present invention. Particularly useful are the analogs and variants disclosed in, e.g., U.S. Pat. Nos. 5,128,242; 5,198,542; 5,208,320; 5,326,860; 5,623,050; 5,801,147 and 6,242,563.

Similarly, EGF variants or analogs, which share a substantial identity with a native mammalian EGF are capable of increasing neural stem cell numbers can be used in the present application. These EGF variants and analogs include, but are not limited to, the recombinant modified EGF having a deletion of the two C-terminal amino acids and a neutral amino acid substitution at position 51, such as asparagine, glutamine, serine or alanine (particularly EGF51N or EGF51Q, having asparagine or glutamine at position 51, respectively; WO 03/040310), the EGF mutein (EGF-$X_{16}$) in which the His residue at position 16 is replaced with a neutral or acidic amino acid (U.S. Pat. No. 6,191,106), the 52-amino acid deletion mutant of EGF at which lacks the amino terminal residue of the native EGF (EGF-D), the EGF deletion mutant in which the N-terminal residue as well as the two C-terminal residues (Arg-Leu) are deleted (EGF-B), the. EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in WO 03/040310, and U.S. Pat. Nos. 6,191,106 and 5,547,935.

Specifically included as prolactins are the naturally occuring prolactin variants, prolactin-related protein, placental lactogens, S179D-human prolactin (Bernichtein et al., 2001), prolactins from various mammalian species, including but not limited to, human, other primates, rat, mouse, sheep, pig, and cattle, and the prolactin mutants described in U.S. Pat. Nos. 6,429,186 and 5,955,346.

Alternatively, neural stem cells can be proliferated in the presence of the oligodendrocyte promoting factor to increase the number of committed oligodendrocyte progenitor cells before being allowed to differentiate.

The oligodendrocytes produced from neural stem cell culture can be introduced (e.g., by transplantation) into a mammal, particularly to compensate for lost or dysfunctional oligodendrocytes. The mammal is preferably a human, canine, feline, rodent, sheep, goat, cattle, horse, pig, or non-human primate. Most preferably, the mammal is human. Since neural stein cells can be cultured from brain tissues from mammals of any age, including adults, it is preferable to grow neural stem cells using a mammal's own tissue for autologous transplantation. Allogeneic and xenogeneic transplantations are also possible, particularly when the transplantation site is in the brain, where immunologic rejection is less severe due to the blood-brain barrier.

It is also contemplated that neural stem cells can be transplanted into a mammal and induced to form oligodendrocytes in vitro. Thus, neural stem cells may be expanded in culture using established methods, transplanted into the mammal, and contacted in vivo with the oligodendrocyte promoting factor to produce oligodendrocytes. Optionally, the transplanted neural stem cells can be expanded again in vivo by administering to the mammal a biological agent that is known to increase the number of neural stem cells as disclosed above.

The cells are preferably introduced into the brain or spinal cord of the mammal, particularly at sites where oligodendrocytes are insufficient, for example, around axons that have been demyelinated. In humans, areas of demyelination are generally associated with plaque like structures, which can be visualized with magnetic resonance imaging (MRI). The cells may also be transplanted into other areas of the central nervous system, as glial cells are known to be able to migrate to their neuronal targets. A particular useful approach is to transplant into the "minor image" location of a target lesion in the other hemisphere, since cells are known to efficiently migrate to the corresponding location in the opposite hemisphere through the corpus callosum (Learish et al., 1999).

The oligodendrocyte promoting factors or the biological agents can be administered by any suitable route established in the art, including, for example, intrathecally, intravascularly, intravenously, intramuscularly, intraperitoneally, transdermally, intradermally, subcutaneously, orally, topically, rectally, vaginally, nasally or by inhalation. The route of administration depends primarily on the nature of the agent. For example, GM-CSF is capable of crossing the blood-brain barrier (McLay et al., 1997), hence it can be administered systemically as well as into the brain. The preferred method of administration is be injection (e.g., with a needle or a catheter) or infusion.

The present invention further provides a method of enhancing oligodendrocyte production in vitro by administering the oligodendrocyte promoting factor to a mammal under conditions that result in oligodendrocyte formation. The resultant oligodendrocytes are capable of remyelinating demyelinated neurons in the mammal, whereby demyelinating diseases in the mammal can be treated or ameliorated. Although previous researchers suggested that GM-CSF may enhance inflammation and degeneration of myelin (Be'eri et al., 1998; Ousman et al., 2001), our results indicate, unexpectedly, that GM-CSF is useful as an oligodendrocyte promoting factor.

It is contemplated that the present invention can also be used to prevent demyelinating diseases where a mammal is at risk of such diseases. Although the causes for multiple sclerosis are not entirely clear, certain risk factors have been identified. For example, multiple sclerosis (MS) occurs in 1-2% of first-degree relatives of MS patients, and people with certain histocompatibility antigens are correlated with MS as well. Therefore, the present invention may be used to prevent MS in the high-risk group.

The GM-CSF useful in the present invention includes any GM-CSF analog or variant that is capable of increasing oligodendrocyte production from neural stem cells. A GM-CSF analog or variant is a polypeptide which contains at least about 30% of the amino acid sequence of the native human GM-CSF, and which possesses a biological activity of GM-CSF. Preferably, the biological activity of GM-CSF is the ability to bind a GM-CSF receptor. Specifically included as GM-CSFs are the naturally occurring GM-CSF proteins and GM-CSFs from various species, including but not limited to, human, canine, feline, rodent, sheep, goat, cattle, equine., swine, or non-human primates.

Besides GM-CSF, other cytokines that have similar biological functions can also be used in lieu of or in addition to GM-CSF as an oligodendrocyte promoting factor in the present invention. These cytokines include granulocyte colony stimulating factor (G-CSF), interleukin-3 (IL-3) and interleukin-5 (IL-5). As with GM-CSF, analogs and variants of G-CSF, IL-3 and IL-5 can also be employed. These G-CSF, IL-3 and IL-5 analogs and variants should share substantial sequence identity with the native human G-CSF, IL-3 and IL-5, respectively, and bind a receptor for G-CSF. IL-3 and IL-5. respectively. The ability of each analog and variant to stimulate production of oligodendrocyte can be determined according to the methods disclosed herein. It is further contemplated that factors known to induce or activate GM-CSF, G-CSF, IL-3 and IL-5 can be employed to promote oligodendrocyte formation and remyelination in accordance with the present disclosure.

In addition to the oligodendrocyte promoting factors described above, other factors known to enhance oligodendrocyte differentiation (see., e.g.. Miller, 2002) can be used in combination with the oligodendrocyte promoting factor(s). These other factors include, without being limited to, Sonic hedgehog, platelet derived growth factor (PDGF), ciliary neurotrophic factor (CNTF), leukemia inhibitory factor (LIF), triiodothyronine (T3), cAMP and retinoic acid. Furthermore, factors that have mitogenic, proliferative or survival effects on oligodendrocytes can also be added, such as neurotrophin 3 (NT-3), growth-related oncogene alpha (GRO-alpha), neuregulin and/or EGF. As with all other factors and agents in the present invention, analogs and variants of these factors that share a substantial sequence identity, and the desired biological activity can also be used.

The following examples ale offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| ° C. = | degree Celsius |
| hr = | hour |
| min = | minute |
| μm = | micromolar |
| mM = | millimolar |
| M = | molar |
| ml = | milliliter |
| μl = | microliter |
| mg = | milligram |

-continued

| | |
|---|---|
| μg = | microgram |
| FBS = | fetal bovine serum |
| PBS = | phosphate buffered saline |
| DMEM = | Dulbecco's modified Eagle's medium |
| α-MEM = | α-modified Eagle's medium |
| MHM = | media hormone mix |
| GM-CSF = | granulocyte-macrophage colony stimulating factor |
| G-CSF = | granulocyte colony stimulating factor |
| IL-3 = | interleukin 3 |
| IL-5 = | interleukin 5 |
| EGF = | epidermal growth factor |
| PDGF = | platelet derived growth factor |
| GalC = | galactocerebroside |
| MBP = | myelin basic protein |
| T3 = | triiodothyronine |
| CNTF = | ciliary neurotrophic factor |
| DIV = | days in vitro |

Example 1

GM-CSF Enhances Oligodendrocyte Production from Neural Stem Cells

To determine the effect of GM-CSF on neural stem cell differentiation, a culture of neural stein cells was prepared from mouse embryos and subjected to a rapid differentiation protocol. Embryonic Day 14 (E14) mouse ganglionic eminence was dissected and grown in media hormone mix (MHM) plus 20 ng/ml epidermal growth factor (EGF) for one week to generate primary neurospheres. The composition of MHM was as follows:

DMEM/F12 (1:1)

glucose (0.6%)

glutamine (2 mM)

sodium bicarbonate (3 M)

HEPES (5 mM)

insulin (25 μg/ml transferrin (100 μg/ml)

progesterone (20 nM)

putrescine (60 μM)

selenium chloride (30 nM)

Primary neurospheres were then dissociated and plated on poly-L-ornithine coated coverslips in 24-well plates at a density of 200,000 cells/ml in 1 ml of MHM per well. Cells were allowed to differentiate in the absence or presence of 20 ng/ml GM-CSF (murine recombinant GM-CSF, Peprotech) in MHM or 20 ng/ml of triiodothyronine (T3, Sigma) in MHM, or in a combination of both GM-CSF and T3. T3 is a known oligodendrocyte differentiation factor, which was used to compare GM-CSF in these experiments.

After 1, 3 or 5 days, the cells were fixed with 4% paraformaldehyde. The cells fixed after 1, 3 and 5 days were immunostained for the immature oligodendrocyte marker O4, the maturing oligodendrocyte marker galactocerebroside (GalC), and the mature oligodendrocyte marker myelin basic protein (MBP), respectively. After staining, the numbers of O4-positive, GalC-positive and MBP-positive cells were counted. The total number of cells were determined using Hoechst staining and live nuclei morphology under 40× magnification. This experiment was performed four times, and 10 non-overlapping fields per coverslip were counted each time. Statistical analyses of the results were performed using Anova with a Tukey-Honest post-hocs analysis. The results are shown in Table 1.

TABLE 1

The Effect of GM-CSF on neural stem cell differentiation

| Antigen | DIV | Control | GM-CSF | T3 | GM-CSF + T3 |
|---|---|---|---|---|---|
| | | | % positive cells | | |
| O4 | 1 | 10.3 ± 0.8 | 16.6 ± 1.2* | 18.2 ± 1.2* | 23.3 ± 2.0*† |
| O4 | 3 | 20.9 ± 1.27 | 25.7 ± 1.5 | 35.9 ± 1.7* | 42.5 ± 2.3*† |
| O4 | 5 | 7.3 ± 0.9 | 9.6 ± 1.0 | 19.9 ± 1.5* | 46.2 ± 2.67*† |
| GalC | 1 | 2.1 ± 0.4 | 4.1 ± 0.6 | 8.0 ± 0.8* | 4.7 ± 0.9* |
| GalC | 3 | 5.2 ± 0.6 | 7.4 ± 0.8 | 15.3 ± 1.5* | 10.4 ± 1.4* |
| GalC | 5 | 3.6 ± 0.6 | 7.9 ± 1.0* | 11.1 ± 0.9* | 9.6 ± 1.1* |
| MBP | 1 | 0.8 ± 0.2 | 1.2 ± 0.3 | 1.6 ± 0.4 | 1.0 ± 0.3 |
| MBP | 3 | 2.4 ± 0.5 | 8.1 ± 0.9* | 13.9 ± 1.1* | 14.1 ± 1.1* |
| MBP | 5 | 2.0 ± 0.5 | 12.2 ± 1.3* | 17.2 ± 1.6* | 16.3 ± 1.7* |

(*$p < 0.05$ as compared to control, †$p < 0.05$ as compared to GM-CSF and T3)

Therefore, GM-CSF significantly increased the percentage of oligodendroyctes in every stage of oligodendrocyte development, indicating that GM-CSF can be used to produce oligodendrocytes more efficiently. Other oligodendrocyte differentiation factors, such as T3, can be optionally employed in combination with GM-CSF.

The effect of GM-CSF was specifically inhibited by GM-CSF receptor alpha (sGMRa), a soluble factor that binds GM-CSF. A rapid differentiation protocol was performed, as described above, in the absence or presence of GM-CSF, with or without a 100-fold excess of sGMRa. After 5 days in vitro, the cells were fixed, immunostained with the mature oligodendrocyte marker MBP and counted as previously described. The results are shown in FIG. 1, which indicates that the effect of GM-CSF was specific.

Example 2

Effect of GM-CSF on Oligodendrocyte Survival

The survival effects of GM-CSF on oligodendrocytes were examined with two lines of experiments. In the first line of experiments, neural stem cells were cultured as described in Example 1 in the presence or absence of GM-CSF or T3, and were fixed after 1, 3 or 5 days of culture in differentiation media. The fixed cells were immunostained for the maturing oligodendrocyte marker GalC and TUNEL, which is a marker of dying cells. The numbers of dicing, maturing oligodendrocytes (GalC+, TUNEL+cells) were then counted and their percentage in total GalC+cells are shown in FIG. 2.

Figure 2:
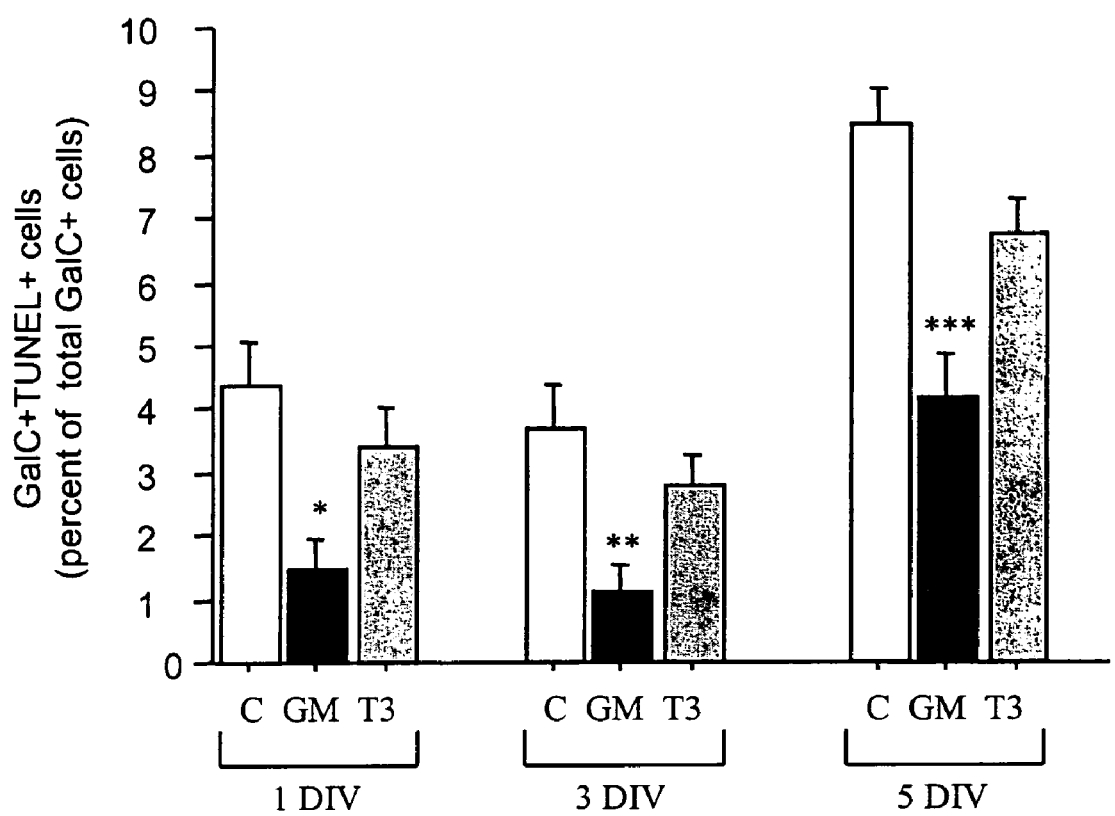
FIG. 2. The percent of dying maturing oligodendrocytes. C: control; GM: GM-CSF; T3: triiodothyronine; DIV: days in vitro. *p<0.05, p<0.01, *p<0.001. The experiments were repeated 4 times (N=4).

As shown in FIG. 2, GM-CSF significantly reduced the number of dying GalC+cells, while T3 had only minor survival effects, if any. This survival effect of GM-CSF was evident after the cells had been in differentiation culture for only one day, and became more prominent with time. Therefore, these results indicate that GM-CSF can act as a survival factor for oligodendrocytes.

In the second line of experiments, GM-CSF ,as given to differentiating neural stem cells at different times. Thus, neural stem cell culture was placed in differentiation media as described in Example 1, and GM-CSF was added after 24 or 48 hours, or added in the beginning but removed after 24 or 48 hours. Similarly, T3 was added or removed in the same manner in parallel experiments. The cells were fixed after 5 days in vitro and immunostained with the mature oligodendrocyte marker MBP. The experiments were performed 4 times (N=4) and the results are shown in Table 2 (*$p<0.05$).

TABLE 2

Survival Assay

| Condition | MBP + cells after 5DIV | |
|---|---|---|
| Control | 2.8 ± 0.3 | |
| GM-CSF added after 24 hours | 8.1 ± 0.9 | ] * |
| GM-CSF added after 48 hours | 3.9 ± 0.6 | |
| GM-CSF removed after 24 hours | 5.4 ± 1.0 | ] * |
| GM-CSF removed after 48 hours | 9.7 ± 1.0 | |
| GM-CSF present for 5 DIV | 8.0 ± 0.8 | |
| T3 added after 24 hours | 14.8 ± 1.5 | |
| T3 added after 48 hours | 12.0 ± 1.1 | |
| T3 removed after 24 hours | 15.5 ± 1.1 | |
| T3 removed after 48 hours | 13.8 ± 1.1 | |
| T3 present for 5 DIV | 13.9 ± 1.1 | |

Therefore, the presence of GM-CSF is required for an extended period of time in order to have an effect on oligodendrocyte numbers, indicating that GM-CSF enhances survival of oligodendrocytes or precursors thereof. In contrast, the, results indicate that T3 acts as a differentiation factor because the number of oligodendrocytes did not chance regardless of the length of time T3 was present in the culture.

Taken together, both lines of experiments indicate that GM-CSF is capable of enhancing survival of oligodendrocytes or precursors thereof.

Example 3

Effect of GM-CSF During Stem Cell Proliferation

To assess the effect of GM-CSF on proliferation of neural stem cells, the number of cells generated in neurosphere cultures, prepared according to Example 1, was counted when grown for 1 week in various culture media. Thus, E14 ganglionic eminence cells were grown at a density of 200,000 cells/ml in 40 ml of media for 1 week. The media were MHM plus EGF, MHM plus EGF and GM-CSF, or MHM plus EGF and T3. Spheres were then collected, dissociated and cells were counted with a hemacytometer. The cell numbers were calculated as percentages of the control (MHM plus EGF).

Figure 3:
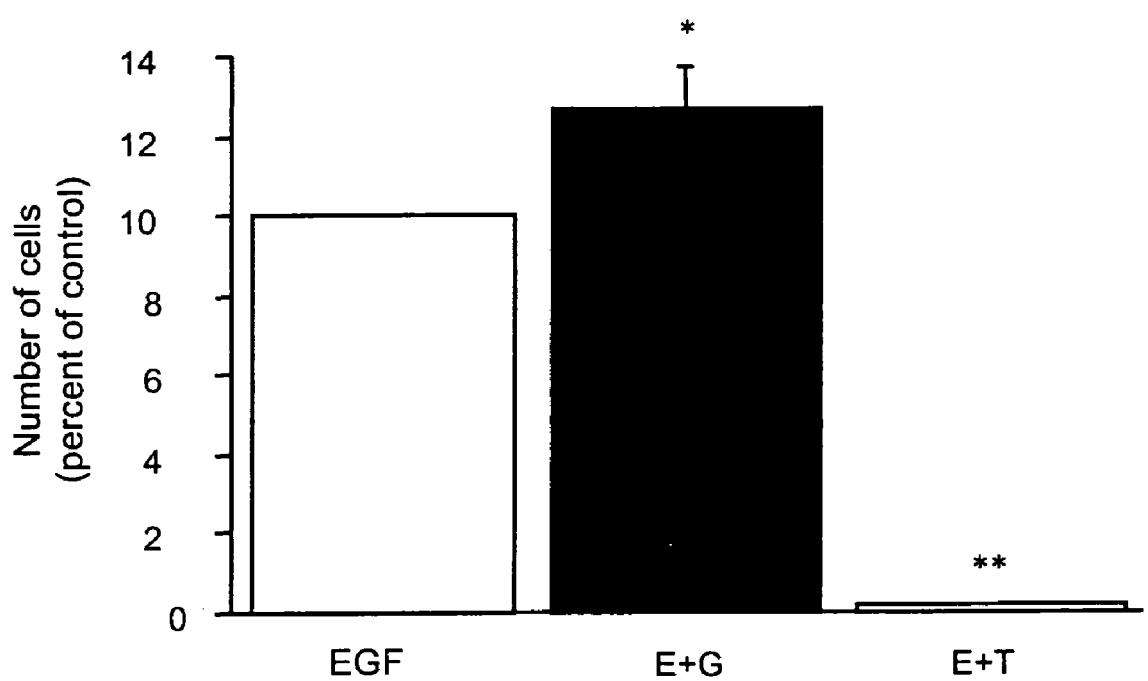
FIG. 3. The effects of GM-CSF (G) and T3 (T) on total cell numbers of primary neural stem cell culture. E+G: EGF+GM−CSF; E+T: EGF+T3. *p<0.05,:** p<0.001. The experiments were carried out 4 times (N=4).

As shown in FIG. 3, these results indicate that GM-CSF slightly increased the total cell number in the neural stem cell culture while T3 reduces the number.

The effect of GM-CSF on primary neurosphere numbers was also examined by growing cells from E14 mouse ganglionic eminence in MHM plus EGF, MHM plus EGF plus GM-CSF, or MHM plus EGF plus T3, all at concentrations of 20 ng/ml. Thus, E14 mouse ganglionic eminence cells were dissociated and plated in 96well plates at a density of 10,000 cells/ml in 200 µl of media per well, and allowed to form primary neurospheres for a week. The number of primary spheres in each well as then counted and the aforementioned statistical analysis as performed.

Figure 4:
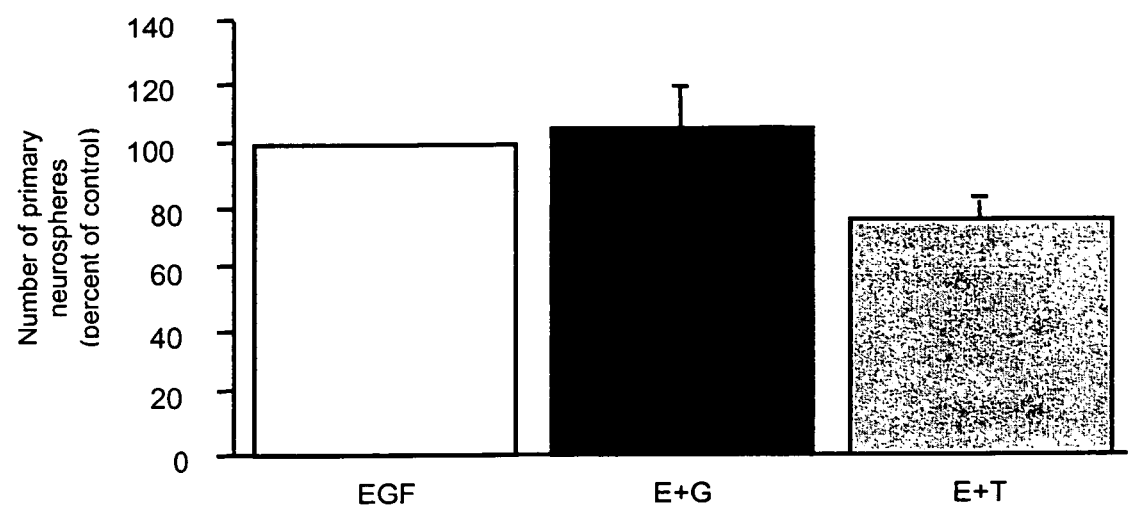
FIG. 4. Primary neurosphere numbers when cultured in various media. E+G: EGF÷GM−CSF; E+T: EGF+T3.

The results, shown in FIG. 4, suggest that neither GM-CSF nor T3 have significant effects on the ability of neural stem cells to form primary neurospheres.

Furthermore, the effect of GM-CSF on self-expansion, proliferation of secondary neurospheres derived from primary neurospheres, was also assessed. Three media were used in the preparation of primary spheres: MHM plus EGF, MHM plus EGF plus GM-CSF and MHM plus EGF plus T3. The primary spheres were dissociated, plated in 96-well plates at a concentration of 1000 cells/well in 200µL media per well, and allowed to form secondary neurospheres for a week. The media for secondary cultures consisted of MHM plus EGF alone, MHM plus GM-CSF or T3 alone, or MHM plus EGF supplemented with GM-CSF or T3. The number of secondary spheres in each well was then counted, calculated as percentage of control (EGF to EGF).

Figure 5:
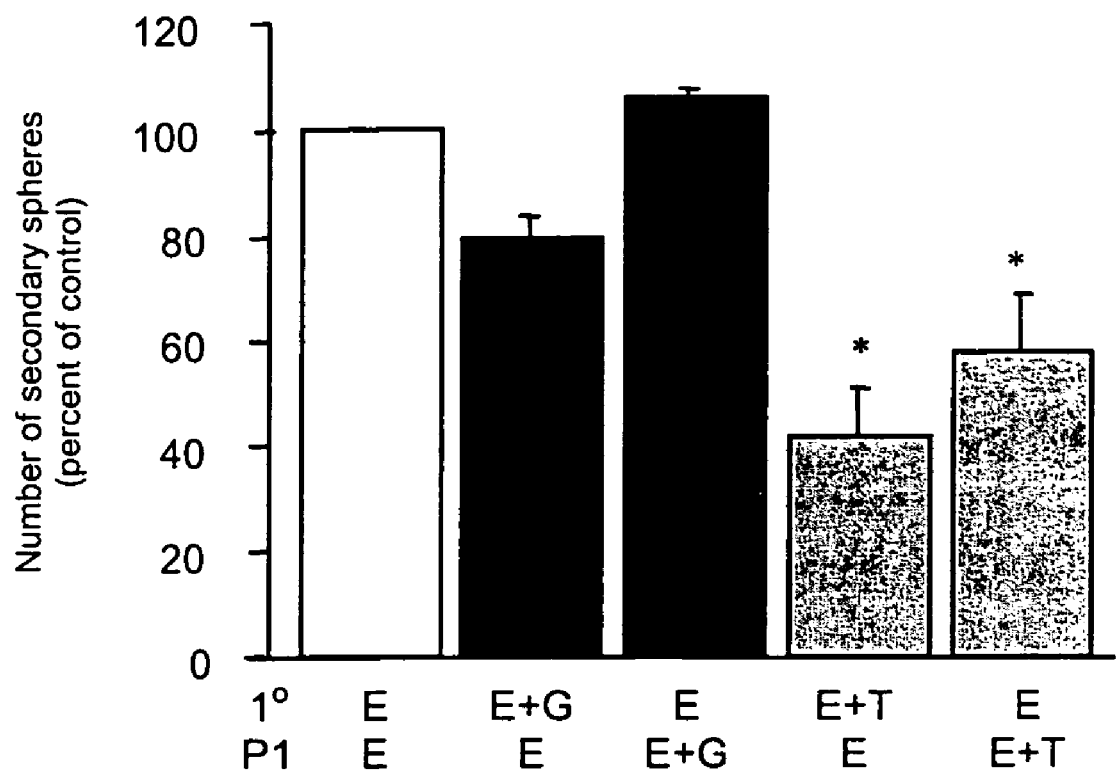
FIG. 5. Secondary neurosphere numbers when cultured in various media. 1°: primary neurosphere media: P1: secondary neurosphere media; E: EGF: E+G: EGF+GM−CSF; E+T: EGF+T3. *p<0.001. The experiments were performed 5 times (N=5).

FIG. 5 shows that GM-CSF does not significantly affect the number of secondary neurospheres derived from EGF-responsive neural stem cells. In addition, T3 decreased the number of secondary neurospheres in this experiment, possibly by enhancing differentiation. The results also indicate that including GM-CSF or T3 in the media for primary neurospheres was detrimental to formation of secondary spheres.

Taken together, these results indicate that GM-CSF does not enhance proliferation or self-expansion of neural stem cells. The increase by GM-CSF of the number of total cells in primary culture may be due to the survival effect of GM-CSF.

Example 4

Effect of GM-CSF on Fate Determination of Neural Stem Cells

To determine if the presence of GM-CSF during primary neurosphere formation impacts fate determination of neural stem cells, primary neurospheres were generated in either EGF alone, EGF plus GM-CSF, or EGF plus T3 as described in Example 3. The primary spheres were then dissociated and plated on poly-L-ornithine coated coverslips in 24-well plates at a density of 200,000 cells/well in 1 ml of MHM per well, and allowed to differentiate for 5 days. At the end the differentiation period, the cells were fixed with 4% paraformaldehyde and immunostained for the mature oligodendrocyte marker MBP, the neuronal marker β-tubulin, and Hoechst. The total number of live cells, evidenced by Hoechst stain, were counted as well as the immunostained cells. The results are shown in FIG. 6.

Figure 6:
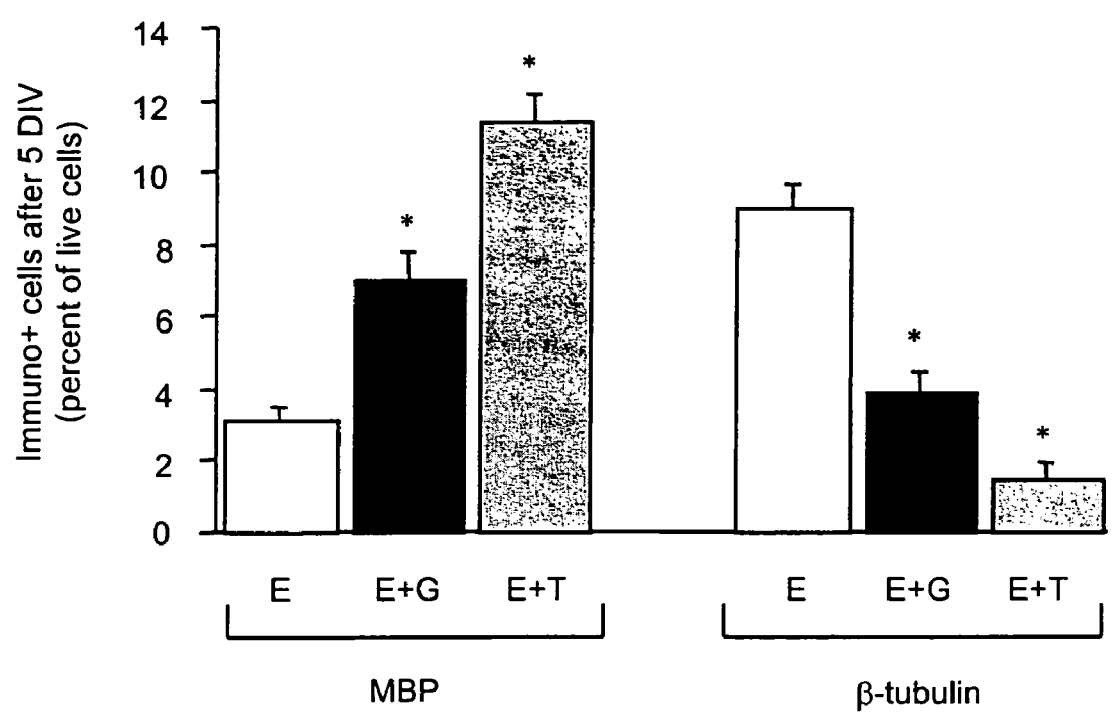
FIG. 6. Fate determination analysis. Mature oligodendrocytes (MBP+cells) or neurons (∃-tubulin+cells) were counted after neural stem cells had been cultured in various media. E: EGF; E+G: EGF+GM-CSF; E+T: EGF+T3. * p<0.05.

As shown in FIG. 6, GM-CSF and T3 increased the number of mature oligodendrocytes and decreased that of neurons. In conjunction with the previous examples, these results indicate that GM-CSF promotes differentiation of oligodendrocytes from neural stem cells and reduces the number of neuronal progenitors, thereby reducing the number of neurons. Therefore, GM-CSF can be used to produce oligodendrocytes by shifting the fate of neural stein cells toward the oligodendrocyte lineage.

I claim:

1. A method of producing oligodendrocytes from mammalian multipotent neural stem cells, comprising:
   providing a cell culture of multipotent neural stem cells obtained from neural tissue;
   contacting the multipotent neural stem cells with an effective amount of granulocyte-macrophage colony stimulating factor (GM-CSF); culturing the multipotent neural stem cells to produce oligodendrocytes,
   wherein the GM-CSF is selected from the group consisting of native human, canine, feline, rodent, sheep, goat, cattle, equine, swine, and non-human primate GM-CSF.

2. The method of claim 1 wherein the cell culture is prepared using mammalian brain tissue.

3. The method of claim 1 wherein the mammalian brain tissue is obtained from a non embryonic mammal.

4. The method of claim 2 wherein the mammalian brain tissue is obtained from an adult mammal.

5. The method of claim 2 wherein the brain tissue is obtained from the subventricular zone.

6. A method of producing oligodendrocytes from mammalian multipotent neural stem cells, comprising;

providing a cell culture of multipotent neural stem cells obtained from neural tissue;

contacting the multipotent neural stem cells with an effective amount of granulocyte-macrophage colony stimulating factor (GM-CSF); culturing the multipotent neural stem cells to produce oligodendrocytes, wherein the GM-CSF is at least 80% identical to native human GM-CSF.

7. The method of claim 6 wherein the cell culture is prepared using mammalian brain tissue.

8. The method of claim 7 wherein the mammalian brain tissue is obtained from a non-embryonic mammal.

9. The method of claim 7 wherein the mammalian brain tissue is obtained from an adult mammal.

10. The method of claim 7 wherein the brain tissue is obtained from the subventricular zone.

11. A method of producing oligodendrocytes from mammalian multipotent neural stem cells, comprising:

providing a cell culture of multipotent neural stem cells obtained from neural tissue;

contacting the multipotent neural stem cells with an effective amount of granulocyte-macrophage colony stimulating factor (GM-CSF); culturing the multipotent neural stem cells to produce oligodendrocytes, wherein the GM-CSF is at least 80% identical to native mouse GM-CSF.

12. The method of claim 11 wherein the cell culture is prepared using mammalian brain tissue.

13. The method of claim 12 wherein the mammalian brain tissue is obtained from a non-embryonic mammal.

14. The method of claim 12 wherein the mammalian brain tissue is obtained from an adult mammal.

15. The method of claim 12 wherein the brain tissue is obtained from the subventricular zone.

* * * * *

UNITED STATES PATENT AND TRADEMARK OFFICE
CERTIFICATE OF CORRECTION

PATENT NO. : 7,704,737 B2 Page 1 of 1
APPLICATION NO. : 10/523253
DATED : April 27, 2010
INVENTOR(S) : Samuel Weiss It is certified that error appears in the above-identified patent and that said Letters Patent is hereby corrected as shown below:

Column 14, line 60, "claim 1" should read
--claim 2--

Signed and Sealed this

Thirty-first Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,704,737 B2 | Page 1 of 1 |
| APPLICATION NO. | : 10/523253 | |
| DATED | : June 22, 2010 | |
| INVENTOR(S) | : Weiss | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 415 days.

Signed and Sealed this

Twenty-third Day of November, 2010

David J. Kappos
*Director of the United States Patent and Trademark Office*